United States Patent
Schlama

(10) Patent No.: US 6,555,697 B1
(45) Date of Patent: Apr. 29, 2003

(54) METHOD OF PREPARING A BENZOFURAN OR BENZOTHIOPHENE COMPOUND

(75) Inventor: Thierry Schlama, Dardilly (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/110,443

(22) PCT Filed: Oct. 23, 2000

(86) PCT No.: PCT/FR00/02947

§ 371 (c)(1), (2), (4) Date: Apr. 11, 2002

(87) PCT Pub. No.: WO01/29019

PCT Pub. Date: Apr. 26, 2001

(30) Foreign Application Priority Data

Oct. 21, 1999 (FR) .............................................. 99 13251
May 24, 2000 (FR) .............................................. 00 06629

(51) Int. Cl.[7] ...................... C07D 307/79; C07D 333/54
(52) U.S. Cl. .......................... 549/471; 549/43; 549/49; 549/51; 549/57; 549/58; 549/459; 549/469
(58) Field of Search ................. 549/471, 459, 549/469, 49, 51, 57, 58, 43

(56) References Cited

U.S. PATENT DOCUMENTS 3,577,441 A    5/1971    Kaminsky ................ 260/346.2

FOREIGN PATENT DOCUMENTS

EP    0 471 609    2/1992    ......... C07D/307/81

OTHER PUBLICATIONS

T. Suzuki: "Benzofuran derivatives. I On the effect of substituents in benzofuran synthesis" Bulletin of the Chemical Society of Japan, vol. 56, No. 9, Sep. 1983, pp. 2762–2767, XP002141555. Tokyo JP. , p. 2762–p. 2764.

W. T. Brady: "Benzofurans. Ketene intermediates in the Perkin reaction" Journal of Heterocyclic Chemistry, vol. 25, 1988, pp. 969–971, XP002141556.

International Search Report.

Primary Examiner—Bernard Dentz

(57) ABSTRACT

The invention concerns a novel method for preparing a benzofuran or benzothiophene compound by cyclizing an aromatic compound bearing a side-chain comprising at least two carbon atoms, one of the carbon atoms being bound to the benzene cycle by an oxygen or sulphur atom, the other carbon atom is in carboxylic form and a formyl radical in ortho position relative to said chain. The inventive method is characterised in that it consists in cyclizing the latter in the presence of an efficient amount of a carbonate base in a medium comprising a carboxylic acid anhydride and optionally an organic solvent.

30 Claims, No Drawings

METHOD OF PREPARING A BENZOFURAN OR BENZOTHIOPHENE COMPOUND

This application is an application under 35 U.S.C. Section 371 of International Application Number PCT/FR00/02947 filed on Oct. 23, 2000.

The present invention relates to a novel process for preparing a benzofuran or benzothiophene type compound by cyclising an aromatic compound carrying firstly, a side chain containing at least two carbon atoms, one of the carbon atoms being connected to the benzene ring via an oxygen or sulphur atom, the other carbon atom being in the carboxylic form, and secondly, carrying a formyl group in the ortho position with respect to said chain.

More particularly, the invention relates to the preparation of 2-n-butyl-5-nitrobenzofuran.

Benzofuran or benzothiophene type structures are encountered in many molecules used in the pharmaceutical field. In particular, European patent EP-A-0 471 609 describes a process for preparing n-butyl-2-nitro-5-benzofuran, which consists of reacting 2-hydroxy-5-nitro-benzyltriphenylphosphonium bromide with pentanoyl chloride in the presence of pyridine: 2-hydroxy-5-nitro-benzyltriphenylphosphonium bromide is obtained from 2-hydroxy-5-nitro-benzyl bromide and triphenylphosphine.

The aim of the present invention is to provide another process for liquid phase preparation that can produce a good yield of 5-nitrobenzofuran.

We have now discovered, and this constitutes the subject matter of the present invention, a process for preparing a benzofuran or benzothiophene type compound from an aromatic compound carrying firstly, a side chain comprising at least two carbon atoms, one of the carbon atoms being connected to the aromatic ring via an oxygen or sulphur atom, the other carbon atom being in the carboxylic form, and secondly, carrying a formyl group in the position ortho to said chain, characterized in that it consists of cyclising the latter, in a medium comprising a carboxylic acid anhydride and in the presence of a base selected from metallic or ammonium carbonates and/or bicarbonates.

A preferred variation of the process of the invention consists of preparing a benzofuran or benzothiophene type compound from an aromatic compound carrying firstly, a side chain comprising at least two carbon atoms, one of the carbon atoms being connected to the aromatic ring via an oxygen or sulphur atom, the other carbon atom being in the carboxylic form, and secondly, carrying a formyl group in the position ortho to said chain, by cyclising the latter in the presence of an effective quantity of a base as defined above, in a medium comprising a carboxylic acid anhydride and in the presence of an organic solvent.

We have discovered that using an organic solvent such as dimethylformamide facilitates recovery of the cyclised product while reducing the quantity of carboxylic acid anhydride employed.

The starting reactant in the process of the invention is an aromatic compound, preferably a benzene compound, carrying a side chain and a formyl group in the position ortho to the side chain.

The side chain has 3 features:
- an oxygen or sulphur atom connects the side chain to the benzene ring;
- 2 carbon atoms connected together included in the 5 atom cycle that also includes the 2 carbon atoms of the benzene ring;
- a carboxylic or thiocarboxylic group in the position β with respect to the oxygen or sulphur atom.

The starting reagent can be depicted as follows:

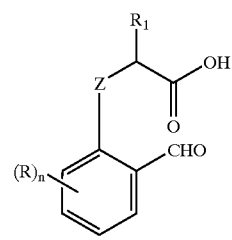

in which formula (I):

$R_1$ represents a hydrogen atom, a linear or branched alkyl group containing 1 to 12 carbon atoms, a phenyl group optionally substituted by an alkyl group containing 1 to 4 carbon atoms, or a halogenophenyl group;

Z represents an oxygen or sulphur atom;

R represents a hydrogen atom or a substituent;

n is a number equal to 0, 1, 2 or 3, preferably 0;

when n is greater than 1, two groups R and the successive 2 atoms of the benzene ring can together form a saturated, unsaturated or aromatic cycle containing 5 to 7 carbon atoms.

In formula (I), the benzene ring may carry a substituent.

The scope of the invention does not exclude the presence on the benzene ring of any type of substituent, provided that it does not react under the conditions of the invention.

More particular examples of group R that can be mentioned include:
- a nitro group;
- a hydroxyl group;
- a linear or branched alkyl group containing 1 to 6 carbon atoms, preferably 1 to 4 carbon atoms, such as methyl, ethyl, propyl, isopropyl, butyl, isobutyl, sec-butyl, tert-butyl;
- an alkoxy group containing 1 to 6 carbon atoms, preferably 1 to 4 carbon atoms;
- an ester group containing 1 to 10 carbon atoms, preferably 1 to 4 carbon atoms;
- an alkylamide group containing 1 to 6 carbon atoms, preferably 1 to 4 carbon atoms;
- a carboxamide group;
- a halogen atom;
- a trifluoromethyl group.

When n is greater than 1, two groups R and the successive 2 atoms of the benzene ring can together form a saturated, unsaturated or aromatic cycle containing 5 to 7 carbon atoms, preferably 6 carbon atoms. Advantageously, two groups R form a benzene ring.

Group $R_1$ is advantageously an alkyl group containing 1 to 4 carbon atoms.

The invention does not exclude the fact that $R_2$ represents a further group such as cycloalkyl, phenyl or arylalkyl, but since group $R_2$ is eliminated, it is important from an economic viewpoint that it should be as simple as possible, for example a lower alkyl group, i.e., containing 1 to 4 carbon atoms. $R_2$ can also represent a hydrogen atom, which corresponds to the presence of a carboxylic group.

Preferred substrates for use in the process of the invention have formula (I) in which R represents a hydrogen atom, a nitro group, methyl or ethyl group, or a methoxy or ethoxy group.

In formula (I), Z preferably represents an oxygen atom.

In formula (I), R can represent a nitro group, preferably in the position meta to the formyl group.

In accordance with the process of the invention, the aromatic compound, preferably with formula (I), is cyclised in the presence of a base selected from metallic or ammonium carbonates and/or bicarbonates.

Suitable bases that can be mentioned in particular are alkali or alkaline-earth metal carbonates and bicarbonates. Caesium carbonate can be used, but preferably, sodium carbonate or potassium carbonate is used.

In accordance with the process of the invention, the aromatic compound, preferably with formula (I), is cyclised in a carboxylic acid anhydride.

More particularly, this latter has the following formula:

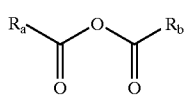

(VI)

in which formula (VI):

$R_a$ and $R_b$, which may be identical or different, represent a monovalent hydrocarbon group that may or may not be substituted, which can be a linear or branched, saturated or unsaturated acyclic aliphatic group; or a monocyclic saturated, unsaturated or aromatic carbocyclic group;

$R_a$ and $R_b$ can together form a divalent linear or branched, saturated or unsaturated aliphatic group containing at least 2 carbon atoms.

Groups $R_a$ and $R_b$ are preferably selected such that the anhydride is liquid under the reaction conditions.

The anhydride used may or may not be cyclic.

More precisely, a cyclic anhydride containing 5 to 10 carbon atoms in the cycle can be used that may or may not contain a double bond, one of the atoms can be replaced by an oxygen atom.

Preferably, the cyclic anhydrides are saturated or contain a double bond and 5 or 6 atoms in the cycle.

The cycle can comprise one or more substituents. More particular examples of substituents that can be cited are linear or branched alkyl groups containing 1 to 12 carbon atoms, preferably 1 to 4 carbon atoms, such as methyl, ethyl, propyl, isopropyl, butyl, isobutyl, sec-butyl, tert-butyl, or halogen atoms or a trihalogenomethyl group.

More particularly, when using a non cyclic anhydride with formula (VI), groups $R_a$ and $R_b$, which may be identical or different, represent:

a linear or branched acyclic aliphatic group preferably containing 1 to 24, more preferably 1 to 12 carbon atoms, which may be saturated or comprise one or more unsaturated bonds in their chain, generally 1 to 3 unsaturated bonds, which may be simple double bonds: the hydrocarbon chain may be interrupted by one of the following groups: —O—; —CO—; and/or carry one or more substituents, in particular: —X; —CX$_3$;

a saturated, unsaturated or aromatic carbocyclic group containing 3 to 8 carbon atoms, preferably 6 carbon atoms, optionally carrying one or more halogen atoms, preferably chlorine or bromine.

Of the groups defined above, $R_a$ and $R_b$ preferably represent:

a linear or branched alkyl group containing 1 to 12 carbon atoms, optionally carrying one or more halogen atoms;

a cyclohexyl or phenyl group, optionally carrying one or more halogen atoms, or a trihalogenomethyl group.

Examples of anhydride that can be cited are:

acetic anhydride;
propanoic anhydride;
isobutyric anhydride;
trichloroacetic anhydride;
trifluoroacetic anhydride;
benzoic anhydride;
monochloroacetyl anhydride;
dichloroacetyl anhydride;
pivalic anhydride.

Acetic anhydride is preferred from the above list of anhydrides.

The invention does not exclude producing the carboxylic anhydride in the medium, from a carboxylic acid.

As mentioned above, in a preferred variation of the process of the invention, an organic solvent is used.

A number of criteria govern the choice of organic solvent.

A first criterion for the organic solvent is that it should be stable in the reaction medium.

A second criterion is that the solvent should have a high boiling point, preferably 50° C. or more.

Examples of solvents that are suitable for use in the present invention that can be cited are aromatic hydrocarbons, which may or may not be halogenated, and aliphatic cycloaliphatic or aromatic ether-oxides.

Examples of aliphatic hydrocarbons that can be cited are aromatic hydrocarbons, more particularly aromatic hydrocarbons such as benzene, toluene, xylenes, cumene, and petroleum cuts constituted by a mixture of alkylbenzenes, in particular Solvesso type cuts.

Regarding aliphatic or aromatic halogenated hydrocarbons, particular mention can be made of dichloromethane, 1,2-dichloroethane and mono- or dichlorobenzene.

The organic solvent can also be an aliphatic, cycloaliphatic or aromatic ether-oxide, more particularly dipropyl oxide, diisopropyl oxide, dibutyl oxide, methyltertiobutylether, ethylene glycol dimethylether (or glyme), diethylene glycol dimethyl ether (diglyme); phenyl oxide; dioxane, and tetrahydrofuran (THF).

Examples of more polar aprotic organic solvents that can also be used in the process of the invention that can be cited are linear or cyclic carboxamides such as N,N-dimethylacetamide (DMAC), N,N-diethylacetamide, dimethylformamide (DMF), diethylformamide or 1-methyl-2-pyrrolidinone (NMP); dimethylsulphoxide (DMSO); hexamethylphosphotriamide (HMPT); tetramethylurea; nitro compounds such as nitromethane, nitroethane, 1-nitropropane, 2-nitropropane or mixtures thereof, nitrobenzene; aliphatic or aromatic nitriles such as acetonitrile, propionitrile, butanenitrile, isobutanenitrile, benzonitrile, benzyl cyanide; tetramethylene sulphone (sulpholane).

It is also possible to use a mixture of solvents.

According to the process of the invention, the starting substrate is cyclised in the presence of a base and a carboxylic acid anhydride.

More precisely, the quantity of base, expressed as the ratio between the number of moles of base and the number of moles of starting substrate, preferably with formula (I), is in the range 0.05 to 1.0 and is preferably in the range 0.1 to 0.2.

The quantity of carboxylic acid anhydride employed is such that the mole ratio of carboxylic acid anhydride/compound with formula (I) is preferably in the range 2 to 10.

In the preferred variation of the process of the invention, which consists of using an organic solvent, the quantity of carboxylic acid anhydride employed is such that the mole ratio of carboxylic acid anhydride/compound with formula (I) is preferably in the range 1 to 3, more preferably in the range 1 to 2.

Regarding the quantity of organic solvent employed, it is determined as a function of the nature of the organic solvent selected.

It is determined such that the concentration of substrate in the organic solvent is preferably in the range 1 to 10 mole/liter, more preferably in the range 2 to 3 mole/liter.

The starting substrate cyclising reaction takes place at a temperature that is advantageously in the range 50° C. to 160° C., preferably in the range 100° C. to 140° C.

The cyclisation reaction is generally carried out at atmospheric pressure but preferably, it is carried out in a controlled inert gas atmosphere. A rare gas atmosphere can be established, preferably with argon, but it is cheaper to use nitrogen.

From a practical viewpoint, the reaction is simple to carry out.

The order in which the reactants are used is not critical. A preferred variation consists of charging the organic solvent, if present, the substrate, the carboxylic anhydride and then the base and heating to the desired temperature.

At the end of the reaction, the cyclised product is obtained, preferably with formula (V) below:

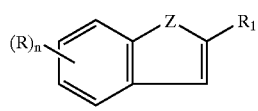

(V)

in which formula (V), R, $R_1$, Y and n have the meanings given above.

The benzofuran or benzothiophene type compound is recovered using conventional techniques, in particular by distillation and/or extraction.

As an example, it is possible to distil the organic solvent if present, also the carboxylic acid anhydride and the carboxylic acid formed.

A solvent for extracting the cyclised compound can then be introduced. More specific examples that can be mentioned are aliphatic or aromatic hydrocarbons, which may or may not be halogenated. Particular examples that can be cited are dichloromethane, dichloroethane, methylcyclohexane and petroleum ether.

The quantity employed is of the same order of magnitude as that of the organic solvent.

The aqueous and organic phases are separated and the latter is treated with a basic aqueous solution, preferably an aqueous solution of dilute sodium hydroxide (5% to 10%) so that the pH is in the range 6 to 8.

One or more washes (for example 3) are carried out, generally finishing with a water wash.

The cyclised product is recovered after eliminating the organic extraction solvent.

The process of the invention is applicable both to known substrates described in the literature and to novel substrates described below and which have the following formula (I'):

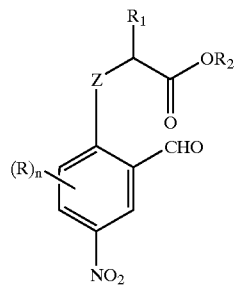

(I')

in which:

$R_1$ represents a linear or branched alkyl group containing 1 to 12 carbon atoms, a phenyl group that may be substituted by an alkyl group containing 1 to 4 carbon atoms, or a halogenophenyl group;

$R_2$ represents a hydrogen atom, a hydrocarbon group containing 1 to 12 carbon atoms, which may be a linear or branched alkyl group, a cycloalkyl group, a phenyl group or a phenylalkyl group;

Z represents an oxygen or sulphur atom;

R represents a hydrogen atom or a substituent;

n is a number equal to 0, 1, 2 or 3, preferably 0;

when n is greater than 1, two groups R and the successive 2 atoms of the benzene ring can together form a saturated, unsaturated or aromatic cycle containing 5 to 7 carbon atoms;

in formula (I'), the benzene ring can carry a substituent. More particularly examples of groups R that can be mentioned include:

a hydroxyl group;

a linear or branched alkyl group containing 1 to 6 carbon atoms, preferably 1 to 4 carbon atoms, such as methyl, ethyl, propyl, isopropyl, butyl, isobutyl, sec-butyl, tert-butyl;

an alkoxy group containing 1 to 6 carbon atoms, preferably 1 to 4 carbon atoms;

an ester group containing 1 to 10 carbon atoms, preferably 1 to 4 carbon atoms;

an alkylamide group containing 1 to 6 carbon atoms, preferably 1 to 4 carbon atoms;

a carboxamide group;

a halogen atom;

a trifluoromethyl group.

Preferred compounds of the process of the invention have formula (I') in which R represents a hydrogen atom, a methyl group or an ethyl group, or a methoxy or ethoxy group.

When n is greater than 1, two groups R and the successive 2 atoms of the benzene ring can together form a saturated, unsaturated or aromatic cycle containing 5 to 7 carbon atoms, preferably 6 carbon atoms. Two groups R then advantageously form a benzene ring.

Group $R_1$ is advantageously an alkyl group containing 1 to 4 carbon atoms.

The invention does not exclude the fact that $R_2$ represents a further group such as cycloalkyl, phenyl or arylalkyl, but since group $R_2$ is eliminated, it is important from an economic viewpoint that it should be as simple as possible, for example a lower alkyl group, i.e., containing 1 to 4 carbon atoms. $R_2$ can also represent a hydrogen atom, which corresponds to the presence of a carboxylic group.

The nitroaromatic compound with formula (I') can be obtained by a process that consists of selectively nitrating, in the 4 position, an aromatic compound with formula (II'):

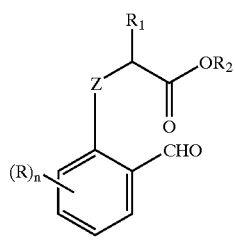

(II')

in which formula (II'), R, $R_1$, $R_2$, Z and n have the meanings given above.

The aromatic compound with formula (II') can be obtained by a process consisting of reacting:

a compound of the 2-hydroxy- or 2-thiobenzaldehyde type with formula (III'):

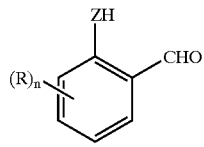

(III')

in which formula (III'), R, Z and n have the meanings given above;

and a carboxylic acid or a derivative with formula (IV):

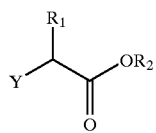

(IV)

in which formula (IV):

Y represents a leaving group, preferably a halogen atom or a sulphonic ester group with formula —$OSO_2$—R where R is a hydrocarbon group;

$R_1$, $R_2$ have the meanings given above.

In the formula for the sulphonic ester group, R is a hydrocarbon group of any nature. However, given that Y is a leaving group, it is important from an economic viewpoint that R should be simple in nature, and more particularly represents a linear or branched alkyl group containing 1 to 4 carbon atoms, preferably a methyl or ethyl group; however, it can also represent a phenyl or tolyl group or a trifluoromethyl group, for example. Preferably, group Y is a triflate group, corresponding to a group R representing a trifluoromethyl group.

Preferred leaving groups that can be selected are halogen atoms, namely bromine, chlorine or iodine, preferably a bromine or chlorine atom.

In accordance with the process of the invention, we start with a novel manufacturing intermediate with formula (I').

It can be obtained using a reaction for selective nitration, in the 4-position, of an O- or S-alkylated compound with formula (II'), by reacting the latter with a source of $NO_2^+$, in the presence of sulphuric acid: the reaction may or may not be carried out in an organic solvent.

To this end, said compound is reacted with a source of $NO_2^+$.

It is possible to start with nitrogen dioxide $NO_2$, nitrous anhydride $N_2O_3$, dinitrogen tetroxide $N_2O_4$, nitric oxide NO associated with an oxidising agent such as nitric acid, nitrogen dioxide or oxygen. When the reactant is gaseous under the reaction conditions, it is bubbled into the medium.

It is also possible to use nitrous acid, a nitrose or nitrosyl sulphate or a nitrous salt, preferably an alkali metal salt, still more preferably sodium associated with an oxidising agent, preferably nitric acid.

It is also possible to use alkyl nitrites associated with an oxidising agent, more particularly those with formula (VII):

$R_a$—ONO (VII)

in which formula (VII), $R_a$ represents a linear or branched alkyl group containing 1 to 12 carbon atoms, preferably 1 to 4 carbon atoms.

The quantity of $NO_2^+$ source is at least equal to the stoichiometric quantity of the O- or S-alkylated aromatic compound. The ratio between the number of moles of $NO_2^+$ source and the number of moles of aromatic O- or S-alkylated compound is advantageously in the range 1.0 to 1.2.

Preferably, a concentrated nitric acid solution is used with a preferred concentration in the range 70% to 99%.

As mentioned above, the $NO_2^+$ source is associated with sulphuric acid.

In a variation, the process of the invention consists of using a nitrating mixture (mixture of nitric acid and sulphuric acid comprising 50% to 98% by weight of nitric acid).

The quantity of nitric acid, expressed as the mole ratio of the O- or S-alkylated aromatic compound/nitric acid, is generally in the range 0.9 to 1.1, preferably in the range 0.95 to 1.05.

The quantity of sulphuric acid, expressed as the mole ratio of the O- or S-alkylated aromatic compound/sulphuric acid, is generally in the range 0.9 to 1.1, preferably in the range 0.95 to 1.05.

The concentration of sulphuric acid is advantageously in the range 50% to 98%.

To this end, nitric acid or a precursor of nitric acid is used, such as dinitrogen tetroxide.

The nitration reaction can optionally be carried out in an organic solvent that is inert under the reaction conditions.

More particular examples of organic solvents that can be cited are aliphatic halogenated hydrocarbons, more particularly perchlorinated hydrocarbons such as tetrachloromethane, hexachloroethane; partially chlorinated hydrocarbons such as dichloromethane, and 1,2-dichloromethane.

Dichloromethane is the preferred solvent.

Regarding the concentration of O- or S-alkylated aromatic compound in the reaction medium, it is preferably in the range 0.2 to 3 mole/l, more preferably in the range 0.3 to 1.5 mole/l.

This is generally introduced in the liquid form.

The reaction is advantageously carried out at a temperature in the range −5° C. to 10° C., and in an inert gas atmosphere.

The process of the invention is generally carried out at atmospheric pressure.

In a preferred variation of the process of the invention, the nitration step is carried out in a controlled inert gas atmosphere. A rare gas atmosphere can be established, preferably argon, but it is cheaper to use nitrogen.

A number of implementations can be envisaged.

In a first variation, the sulphuric acid solution is charged first, followed by the O- or S-alkylated aromatic compound and the nitric acid at the same time.

In a further variation, the sulphuric acid and nitric acid solution is introduced then the O- or S-alkylated aromatic compound is added, preferably in portions, or it is poured in continuously.

In a further variation, the O- or S-alkylated aromatic compound is introduced into a base stock on the one hand and the sulphuric and nitric acid on the other hand.

The reaction advantageously lasts 3 to 10 hours.

At the end of the reaction, the desired product with formula (I') is obtained.

The product is recovered using conventional techniques employed in the field.

In particular, water hydrolysis can be carried out, preferably using ice employed in an amount of 100% to 150% by weight of the compound with formula (I'), for example.

A solid is obtained that is separated using conventional solid/liquid separation techniques, preferably by filtering.

The desired product is then produced.

The compound with formula (II') involved in the preparation of the compound with formula (I') can be obtained using an O- or S-alkylation reaction of a compound of the 2-hydroxy or 2-thiobenzaldehyde type with formula (III') with a carboxylic acid or a derivative with formula (IV).

One implementation consists of reacting an aromatic compound with formula (III') with a carboxylic acid or a derivative with formula (IV): the reaction is carried out in the presence of a base, preferably in an organic solvent.

Of the compounds with formula (III'), salicylic aldehyde is preferred.

A Regarding the compound with formula (IV), methyl or ethyl 2-bromohexanoate is preferably used.

The mole ratio between the compound with formula (III') and the compound with formula (IV) is advantageously between 1 and 1.2.

In accordance with the process of the invention, the 2-hydroxy or 2-thiobenzaldehyde type compound with formula (III') is reacted in its salt form with the carboxylic acid or derivative with formula (IV) in an organic solvent as defined above.

A salt form of a 2-hydroxy or 2-thiobenzaldehyde type compound that has been extemporaneously prepared can be used, but it is also possible to prepare it in situ by reacting the compound of the 2-hydroxy or 2-thiobenzaldehyde type compound and the base.

Thus, a base, which can be mineral or organic, is used in the process of the invention.

Particularly suitable bases for use in carrying out the process of the invention are mineral bases such as alkali metal or alkaline-earth metal salts, preferably an alkali or alkaline-earth metal hydroxide, which may be sodium, potassium or calcium hydroxide; or an alkali metal carbonate or bicarbonate, preferably sodium carbonate.

It is also possible to use an organic base such as a quaternary ammonium hydroxide or an amine.

Preferred examples of quaternary ammonium hydroxides that can be used are tetraalkylammonium or trialkylbenzylammonium hydroxides in which the alkyl groups, which may be identical or different, represent a linear or branched alkyl chain containing 1 to 12 carbon atoms, preferably 1 to 6 carbon atoms.

Preferably, tetramethylammonium hydroxide, tetraethylammonium hydroxide or tetrabutylammonium hydroxide is used.

It is also possible to use trialkylbenzylammonium hydroxides, in particular trimethylbenzylammonium hydroxide.

Examples of amines that can be mentioned include tertiary amines.

Suitable bases that can be cited are tertiary amines, more particularly those with general formula (VIII):

in which:
groups $R_3$, which may be identical or different, represent hydrocarbon residues containing 1 to 20 carbon atoms, such as alkyl, cycloalkyl, aryl or heterocyclic groups;

2 groups $R_3$ together with the nitrogen atom form a heterocycle containing 4 to 6 atoms.

More particularly:
symbols $R_3$ represent an alkyl group containing 1 to 10 carbon atoms, preferably 1 to 4 carbon atoms, or a cyclopentyl or cyclohexyl group or pyridinyl group;

2 groups $R_3$ together form a piperidine or pyrrolidine cycle with the nitrogen atom.

Examples of such amines that can be cited are triethylamine, tri-n-propylamine, tri-n-butylamine, methyldibutylamine, methyldicyclohexylamine, ethyldiisopropylamine, N,N-diethylcyclohexylamine, dimethylamino-4-pyridine, N-methylpiperidine, N-ethylpiperidine, N-n-butylpiperidine, 1,2-dimethylpiperidine, N-methylpyrrolidine, and 1,2-dimethylpyrrolidine.

For reasons of economy, sodium or potassium carbonate are preferred.

While the base is used in its solid form, it is also possible to use the base in solution. The concentration of the starting base solution is not critical. The alkali metal hydroxide solution is employed in a concentration that is generally in the range 10% to 50% by weight.

The quantity of base introduced into the reaction medium takes into account the quantity necessary to change the hydroxyl or thiol function of the 2-hydroxy or 2-thiobenzaldehyde type compound into the salt form.

Generally, the quantity of base, expressed with respect to the 2-hydroxy or 2-thiobenzaldehyde type compound, is in the range 90% to 120% of the stoichiometric quantity.

The hydroxyl or thiol group of the starting substrate with formula (III') is optionally transformed into its salt form in an initial step. Thus, the compound with formula (III') can be transformed into its salt form either by introducing the base then causing it to react at a temperature that is advantageously in the range 0° C. to 100° C., preferably in the range 25° C. to 50° C., or by introducing the base at the same time as the compound with formula (IV).

In accordance with the invention, the O- or S-alkylation reaction is advantageously carried out in the liquid phase comprising the compound with formula (III') and the compound with formula (IV), in the presence of a base.

One of the starting reactants can act as the reaction solvent, but it is also possible to use an organic solvent.

An organic solvent is selected that is less activated than the starting substrate and which preferably dissolves it.

Examples of solvents that are suitable for use in the present invention that can be cited are aromatic hydrocarbons, which may or may not be halogenated, and aliphatic, cycloaliphatic or aromatic ether-oxides. Examples of such solvents have been given above.

Examples of more polar aprotic organic solvents that can also be used in the process of the invention that can be cited are aliphatic or aromatic nitriles such as acetonitrile, propionitrile or benzonitrile, linear or cyclic carboxamides such as N,N-dimethylacetamide (DMAC), dimethylformamide (DMF), diethylformamide or 1-methyl-2-pyrrolidinone (NMP).

Preferred solvents are DMAC or DMF.

It is also possible to use a mixture of organic solvents.

Regarding the concentration of the 2-hydroxy or 2-thiobenzaldehyde type compound in the reaction medium, it is preferably in the range 2% to 50% by weight.

In a variation of the process of the invention, iodine ions are added to accelerate the reaction. Alkali metal iodides can in particular be used, preferably potassium iodide or tetraalkylammonium iodides, preferably tetrabutylammonium iodide.

The quantity of iodide used, expressed as the ratio between the number of moles of iodine salt and the number of moles of compound with formula (III'), can be in the range 0.05 to 0.2.

The temperature for reacting the aromatic compound with formula (III') with a carboxylic acid or derivative with formula (IV) is advantageously in the range 0° C. to 100° C., preferably in the range 25° C. to 50° C.

The reaction generally takes place at atmospheric pressure.

In a preferred variation of the process of the invention, the process of the invention is carried out in a controlled atmosphere of inert gases. A rare gas atmosphere can be established, preferably with argon, but it is cheaper to use nitrogen.

From a practical view point, the process is simple to carry out.

One implementation of the invention consists of charging all of the reactants, the base, the organic solvent and optionally the iodide ions.

The medium is then heated to the selected reaction temperature.

As mentioned above, salt formation can be carried out in a previous step and the compound with formula (III'), the base and the organic solvent can be introduced, the medium is heated to the selected temperature then the compound with formula (IV) is added along with the optional iodide ions, then heated.

The desired product with formula (II') is obtained.

The product obtained is recovered conventionally.

As an example, the salts formed during the reaction can be eliminated by adding water and extracting the product in the organic phase, in a suitable solvent, for example isopropyl ether.

The organic solvent can be eliminated conventionally by evaporation.

The compound with formula (I') is cyclised using the process of the invention to obtain a heterocyclic compound with general formula (V'):

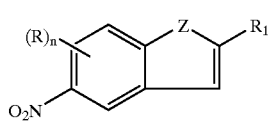

(V')

in which formula (V'), R, $R_1$, Z and n have the meanings given above.

When the compound with formula (I') comprises, as the $COOR_2$ group, an ester function instead of a carboxylic function, a saponification step must initially be carried out before cyclisation. In a further variation, it is possible to carry out saponification, if necessary, of the compound with formula (II') prior to the nitration operation in the same manner.

To this end, the compound with formula (I') is reacted with a base in a hydro-organic medium.

A preferred base is sodium hydroxide or potassium hydroxide, used in the form of flakes concentrated solutions, for example 40% for sodium hydroxide.

The quantity of base employed, expressed as the ratio between the number of moles of compound with formula (I') and the number of moles of base, is preferably between 1 and 5, more preferably between 1 and 2.

The base is dissolved in an aqueous or hydroorganic medium.

Preferably, a polar organic solvent is used.

More particular examples of suitable organic solvents that can be cited are aliphatic alcohols such as ethanol, propanol, butanol, pentanol, ethylene glycol; cycloaliphatic alcohols, in particular cyclohexanol, and arylaliphatic alcohols, more particularly benzyl alcohol. It is also possible to envisage the monomethyl, monoethyl, monopropyl, monobutyl ethers of ethylene glycol sold under the trade name Cellosolves®.

The concentration of compound with formula (I') in the reaction medium (water+organic solvents) advantageously varies between 5% and 50%, preferably in the range 5% to 20% by weight.

The volume ratio between the organic solvent and water can, for example, be between 0.1 and 0.9, preferably in the range 0.1 to 0.2.

The choice of organic solvent and the water/organic solvent ratio is determined so that the solution obtained is homogeneous.

The saponification reaction is carried out at a temperature in the range from ambient temperature to the reflux temperature of the reaction mixture, preferably at a temperature close to 50° C. The term "ambient temperature" generally means a temperature in the range 15° C. to 25° C.

In one practical implementation of the invention, the compound with formula (I') is introduced into the aqueous or hydro-organic medium then the base is added, and the reaction mixture is heated to the selected temperature.

At the end of the reaction, the excess base is neutralised by an acidic solution, preferably a solution of a mineral acid or a mineral salt such as hydrochloric acid or ammonium chloride.

The product obtained precipitates out then it is separated using conventional solid/liquid separation techniques, preferably by filtering.

The cyclisation of the invention is then carried out.

A benzofuran or benzothiophene type derivative nitrated in the 5 position is obtained that has formula (V').

The process of the invention is particularly suitable for preparing 2-n-butyl-5-nitrobenzofuran.

Examples of implementations of the invention will now be given. The examples are given by way of illustration and are not limiting in nature.

EXAMPLE 1

Preparation of 5-nitro-2-butylbenzofuran 23.4 g of 2-(2-formyl-4-nitro-phenoxy)hexanoic acid and 2.3 g of potassium carbonate were charged into a 200 ml reactor containing 80 g of acetic anhydride.

The reaction mixture was heated to reflux in a nitrogen atmosphere to a temperature of close to 130° C. for 5 hours.

After cooling to a temperature of close to 25° C., the medium was extracted with 15 times 50 ml of petroleum ether (40–65° C.).

The combined organic phases were washed with 300 ml of an aqueous sodium bicarbonate solution (10%) and dried over magnesium sulphate.

After evaporating off the solvents under reduced pressure, 11.2 g of 5-nitro-2-butylbenzofuran (Yld by weight=62%) in the form of a yellow oil (NMR purity=95%).

It had the following NMR spectrum:

$^1$H NMR (DMSO-d6): δ 0.91 (t, 3H, CH$_3$); 1.37 (m, 2H, CH$_2$—CH$_3$); 1.67 (m, 2H, CH$_2$—CH$_2$—CH$_3$); 2.81 (m, 2H, CH$_2$—C=); 6.81 (s, 1H, CH=); 7.71 (d, J=9 Hz, 1H, ArH); 8.12 (dd, J=9 Hz, J=2.5 Hz, 1H, ArH); 8.47 (d, J=2.5 Hz, 1H, ArH). The product purity was estimated to be more than 95 mole %.

EXAMPLE 2

Preparation of 5-nitro-2-butylbenzofuran in the presence of an organic solvent 15.3 g of acetic anhydride (0.15 mole) and 2.63 g of potassium carbonate (0.019 mole) were charged into a 200 ml reactor containing 40.9 g of dimethylformamide and 25.1 g of 2-(2-formyl-4-nitro-phenoxy)hexanoic acid (0.1 mole).

The reaction mixture was heated in a nitrogen atmosphere to a temperature of close to 135° C. for 5 hours.

After cooling to a temperature of close to 25° C., the medium was progressively heated between 40° C. and 120° C. under 23 mbar to distil off the dimethylformamide, the acetic acid and the acetic anhydride.

A thick but stirrable reaction mass remained in the reactor.

50 ml of dichloromethane was added to this medium.

It was washed successively with 3 times 25 ml of an aqueous 5% sodium hydroxide solution then 25 ml of water.

The dichloromethane was distilled off at atmospheric pressure to produce 15.8 g of 5-nitro-2-butylbenzofuran (Yld by weight=72.1%) in the form of a yellow oil The purity, determined by NMR, was 95%, and by gas chromatography, it was 99.6%.

It had the following NMR spectrum:

$^1$H NMR (DMSO-d6): δ 0.91 (t, 3H, CH$_3$); 1.37 (m, 2H, CH$_2$—CH$_3$); 1.67 (m, 2H, CH$_2$—CH$_2$—CH$_3$); 2.81 (m, 2H, CH$_2$—C=); 6.81 (s, 1H, CH=); 7.71 (d, J=9 Hz, 1H, ArH); 8.12 (dd, J=9 Hz, J=2.5 Hz, 1H, ArH); 8.47 (d, J=2.5 Hz, 1H, ArH).

EXAMPLE 3

Preparation of 2-(2-formyl-4-nitro-phenoxy)-hexanoic acid 2-(2-formyl-4-nitro-phenoxy)-hexanoic acid can be prepared as follows:

29.5 g of methyl 2-(2-formyl-4-nitro-phenoxy)-hexanoate and 148 ml of water were charged in succession into a 250 ml four-neck reactor provided with a Teflon half moon paddle stirrer, a thermometer, a 50 ml dropping funnel, a cooling coil and a nitrogen inlet.

8.4 g of an aqueous 50% sodium hydroxide solution was added over 20 minutes.

After stirring for 15 minutes at a temperature of close to 25° C., the reaction medium was heated for 2 hours to about 50° C.

The clear red medium obtained was partially evaporated (50 ml) under reduced pressure (20 mm Hg) to eliminate the methanol formed then rediluted with 50 ml of water.

The pH of the reaction medium was brought to about 1.8 by slowly adding 10.8 g of concentrated hydrochloric acid, keeping the temperature to close to 45° C. by stirring.

After stirring for one hour, the temperature of the medium was raised to close to 55° C. for 20 minutes then left at ambient temperature for 12 hours.

The solid product was separated by filtering through a n°3 glass frit and washed with twice 50 ml of water and oven dried for 12 hours at a temperature of close to 55° C.

26.8 g of 2-(2-formyl-4-nitro-phenoxy)-hexanoic acid was obtained in the form of a pale yellow solid melting at 110–111° C. and titrating at 97.5% by potentiometric assay.

It had the following NMR spectrum:

$^1$H NMR (DMSO-d6): δ 0.91 (t, 3H, CH$_3$); 1.38 (m, 2H, CH$_2$—CH$_3$); 1.51 (m, 2H, CH$_2$—CH$_2$—CH$_3$); 2.02 (m, 2H, CH$_2$—CH); 5.24 (t, 1H, CH); 7.34 (d, J=9 Hz, 1H, ArH); 8.44 (dd, J=2 Hz, 1H, ArH); 8.47 (d, J=9 Hz, J=2 Hz, 1H, ArH); 10.42 (s, 1H, CHO); 13.45 (broad peak, 1H, COOH).

EXAMPLE 4

Preparation of 2-(2-formyl-4-phenoxy)-hexanoic acid 2-(2-formyl-4-phenoxy)-hexanoic acid can be prepared as follows:

29.5 g of methyl 2-(2-formyl-phenoxy)-hexanoate and 148 ml of water were charged in succession into a 250 ml four-neck reactor provided with a Teflon half moon paddle stirrer, a thermometer, a 50 ml dropping funnel, a cooling coil and a nitrogen inlet.

10.4 g of an aqueous 50% sodium hydroxide solution was added over 20 minutes.

After stirring for 15 minutes at a temperature of close to 25° C., the reaction medium was heated for 2 hours to about 50° C.

The clear medium obtained was partially evaporated (50 ml) under reduced pressure (20 mm Hg) to eliminate the methanol formed, then re-diluted with 50 ml of water.

The pH of the reaction medium was brought to about 1.8 by slowly adding 10.8 g of concentrated hydrochloric acid, keeping the temperature to close to 45° C. by stirring.

After stirring for one hour, the temperature of the medium was raised to close to 55° C. for 20 minutes then left at ambient temperature for 12 hours.

The solid product was separated by filtering through a n°3 glass frit and washed with twice 50 ml of water then oven dried for 12 hours at a temperature of close to 55° C.

27.4 g of 2-(2-formyl-phenoxy)-hexanoic acid was obtained in the form of a pale yellow solid titrating at 98% by potentiometric assay.

EXAMPLE 5

Preparation of methyl 2-(2-formyl-4-nitro-phenoxy)-hexanoate

Methyl 2-(2-formyl-4-nitro-phenoxy)-hexanoate can be prepared as follows:

123 g of 96% concentrated sulphuric acid was charged into a 250 ml four-neck reactor provided with a Teflon half moon paddle stirrer, a thermometer, a 50 ml dropping funnel, a cooling coil and a nitrogen inlet.

The reaction medium was cooled to a temperature of close to 5° C. then 30 g (0.12 mole) of methyl 2-(2-formylphenoxy)-hexanoate was added at the same temperature.

After stirring for 15 minutes, 15.9 g (0.126 mole) of nitrating mixture (50/50) was added over 2 hours, keeping the reaction medium close to 5° C., then 76.9 g of ice was added over 30 minutes, leading to an $H_2SO_4$ titre of 60%.

The reaction mixture was filtered through a n°3 frit after stirring for 10 minutes.

The crude product obtained was dissolved in 100 ml of dichloromethane and washed with twice 50 ml of water.

The decanted organic phase was concentrated in a rotary evaporator at 20° C. to 70° C. in 20 mm of mercury (duration: 2 hours).

32.7 g of a beige yellow solid product was obtained, giving a yield of methyl 2-(2-formyl-4-nitro-phenoxy)-hexanoate of 92.4%, titrating at 96.7% by gas chromatography.

It had the following NMR spectrum:

$^1H$ NMR (DMSO-d6): δ 0.91 (t, 3H; $CH_3$); 1.38 (m, 2H, $CH_2$—$CH_3$); 1.51 (m, 2H, $CH_2$—$CH_2$—$CH_3$); 2.02 (m, 2H, $CH_2$—CH); 5.24 (t, 1H, CH); 7.34 (d, J=9 Hz, 1H, ArH); 8.44 (d, J=2 Hz, 1H, ArH); 8.47 (dd, J=9 Hz, J=2 Hz, 1H, ArH); 10.42 (s, 1H, CHO); 13.45 (broad peak, 1H, COOH).

EXAMPLE 6

Preparation of 2-(2-formyl-4-nitro-phenoxy)-hexanoic acid 2-(2-formyl-4-nitro-phenoxy)-hexanoic acid can be prepared as follows:

123 g of 96% concentrated sulphuric acid was charged into a 250 ml four-neck reactor provided with a Teflon half moon paddle stirrer, a thermometer, a 50 ml dropping funnel, a cooling coil and a nitrogen inlet.

The reaction medium was cooled to a temperature of close to 5° C. then 28.4 g (0.12 mole) of 2-(2-formylphenoxy)-hexanoic acid was added at the same temperature.

After stirring for 15 minutes, 15.9 g (0.126 mole) of nitrating mixture 50/50 was added over 2 hours, keeping the reaction medium close to 5° C., then 76.9 g of ice was added over 30 minutes, leading to an $H_2SO_4$ titre of 60%.

The reaction mixture was filtered through a n°3 frit.

The solid obtained was dissolved in 100 ml of dichloromethane and washed with twice 50 ml of water.

The decanted organic phase was concentrated in a rotary evaporator at 20° C. to 70° C. in 20 mm of mercury (duration: 2 hours). 32.1 g of a beige yellow solid product was obtained, giving a yield of methyl 2-(2-formyl-4-nitro-phenoxy)-hexanoate of 95%, titrating at 97.0% by gas chromatography.

It had the following NMR spectrum:

$^1H$ NMR (DMSO-d6): δ 0.91 (t, 3H; $CH_3$); 1.38 (m, 2H, $CH_2$—$CH_3$); 1.51 (m, 2H, $CH_2$—$CH_2$—$CH_3$); 2.02 (m, 2H, $CH_2$—CH); 5.24 (t, 1H, CH); 7.34 (d, J=9 Hz, 1H, ArH); 8.44 (d, J=2 Hz, 1H, ArH); 8.47 (dd, J=9 Hz, J=2 Hz, 1H, ArH); 10.42 (s, 1H, CHO); 13.45 (broad peak, 1H, COOH).

EXAMPLE 7

Preparation of methyl 2-(2-formylphenoxy)-hexanoate

Methyl 2-(2-formylphenoxy)-hexanoate can be prepared as follows:

87.1 g (0.714 mole) of salicylic aldehyde, 158.2 g (0.756 mole) of methyl 2-bromohexanoate, 103.5 g (0.75 mole) of potassium carbonate and 5.9 g (0.0355 mole) of potassium iodide were charged in succession into a 1 liter four-neck flask provided with a half moon paddle stirrer, a thermometer, a cooling coil and a 500 ml dropping funnel.

400 g of dimethylformamide was added and the mixture was heated with stirring at a temperature of close to 80° C. for 4 hours.

After cooling to a temperature of close to 25° C., the reaction mixture was filtered through a n°3 glass frit and washed with 50 g of dimethylformamide.

The filtrate was concentrated by evaporation under reduced pressure (25–40 mbars) then diluted with 100 ml of water and successively extracted with a 100 ml batch of dichloromethane then 50 ml of dichloromethane.

The combined organic phases were washed with 50 ml of water and concentrated to dryness by evaporation under reduced pressure.

176.1 g of a clear yellow liquid was obtained, corresponding to a yield of 98.6% of methyl 2-[2-(formylphenoxy)]-hexanoate, titrating at 99.6% pure using gas chromatography.

EXAMPLE 8

Preparation of methyl 2-(2-formylphenoxy)-hexanoate

Methyl 2-(2-formylphenoxy)-hexanoate can be prepared as follows:

130.6 g (1.071 mole) of salicylic aldehyde, 237.3 g (1.134 mole) of methyl 2-bromohexanoate and 155.2 g (1.125 mole) of potassium carbonate were charged in succession into a 2 liter four-neck flask provided with a half moon paddle stirrer, a thermometer, a cooling coil and a 1000 ml dropping funnel.

600 g of dimethylformamide was added and the mixture was heated with stirring to a temperature of close to 80° C. for 4 hours.

After cooling to a temperature of close to 25° C., the reaction mixture was filtered through a n°3 glass frit and washed with 75 g of dimethylformamide.

The filtrate was concentrated by evaporation under reduced pressure (25–40 mbars) then diluted with 150 ml of water and successively extracted with a 150 ml batch of dichloromethane then 75 ml of dichloromethane.

The combined organic phases were washed with 75 ml of water and concentrated to dryness by evaporation under reduced pressure.

265 g of a clear yellow liquid was obtained, corresponding to a yield of 98.9% of methyl 2-[2-(formylphenoxy)]-hexanoate, titrating at 99.6% pure using gas chromatography.

What is claimed is:

1. A process for preparing a benzofuran or benzothiophene compound from a starting aromatic compound comprising a benzene ring, carrying firstly, a side chain comprising at least two carbon atoms, one of the carbon atoms being connected to the benzene ring via an oxygen or sulfur atom, the other carbon atom being in a carboxylic form, and secondly, a formyl group in the position ortho to said side chain, said process comprising the step of cyclising the starting aromatic compound in a medium comprising a carboxylic acid anhydride, in the presence of a base being a metallic carbonate, a metallic bicarbonate, an ammonium carbonate, or an ammonium bicarbonate.

2. A process according to claim 1, wherein the starting aromatic compound has the following formula:

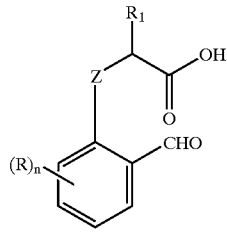

(I)

wherein:
R₁ represents a hydrogen atom, a linear or branched alkyl group containing 1 to 12 carbon atoms, a phenyl group optionally substituted by an alkyl group containing 1 to 4 carbon atoms, or a halogenophenyl group;

Z represents an oxygen or sulfur atom;

R represents a hydrogen atom or a substituent;

n is a number equal to 0, 1, 2 or 3; and when n is greater than 1, two groups R and the successive 2 atoms of the benzene ring can together form a saturated, unsaturated or aromatic cycle containing 5 to 7 carbon atoms.

3. A process according to claim 2, wherein R represents a hydrogen atom or a group selected form the group consisting of the following groups:
   a nitro group;
   a hydroxyl group;
   a linear or branched alkyl group containing 1 to 6 carbon atoms;
   an alkoxy group containing 1 to 6 carbon atoms;
   an ester group containing 1 to 10 carbon atoms;
   an alkylamide group containing 1 to 6 carbon atoms;
   a carboxamide group;
   a halogen atom; and
   a trifluoromethyl group.

4. A process according to claim 3, wherein R represents a methyl, ethyl, propyl, isopropyl, butyl, isobutyl, sec-butyl, or tert-butyl group.

5. A process according to claim 1, wherein the starting aromatic compound has the following formula:

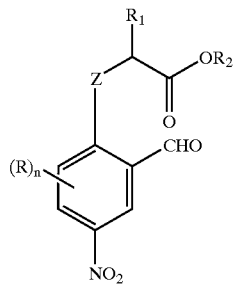

(I')

wherein:
R₁ represents a linear or branched alkyl group containing 1 to 12 carbon atoms, a phenyl group optionally substituted by an alkyl group containing 1 to 4 carbon atoms, or a halogenophenyl group;

R₂ represents a hydrogen atom, or a hydrocarbon group containing 1 to 12 carbon atoms, being a linear or branched alkyl group, a cycloalkyl group, a phenyl group or a phenylalkyl group;

Z represents an oxygen or sulfur atom;

R represents a hydrogen atom or a substituent;

n is a number equal to 0, 1, 2 or 3; and when n is greater than 1, two groups R and the successive 2 atoms of the benzene ring can together form a saturated, unsaturated or aromatic cycle containing 5 to 7 carbon atoms.

6. A process according to claim 2, wherein R represents a hydrogen atom, a methyl group, an ethyl group, a methoxy group or an ethoxy group.

7. A process according to claim 5, wherein R represents a hydrogen atom, a methyl group, an ethyl group, a methoxy group or an ethoxy group.

8. A process according to claim 2, wherein R₁ represents an alkyl group containing 1 to 4 carbon atoms.

9. A process according to claim 1, wherein the base is sodium carbonate or potassium carbonate.

10. A process according to claim 1, wherein the carboxylic acid anhydride has the following formula:

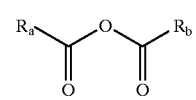

(VI)

wherein:
R$_a$ and R$_b$, which are identical or different, represent a monovalent hydrocarbon group being optionally a substituted, a linear or branched, saturated or unsaturated, acyclic aliphatic group, or a monocyclic saturated, unsaturated or aromatic carbocyclic group;

R$_a$ and R$_b$ can together form a divalent linear or branched, saturated or unsaturated aliphatic group containing at least 2 carbon atoms.

11. A process according to claim 10, wherein the carboxylic acid anhydride is a cyclic anhydride comprising 5 to 10 carbon atoms in the cycle, optionally comprising a double bond, one of the atoms being optionally replaced by an oxygen atom.

12. A process according to claim 10, wherein the carboxylic acid anhydride is a non cyclic anhydride wherein groups R$_a$ and R$_b$, which are identical or different, represent:
   a linear or branched acyclic aliphatic group, saturated or comprising one or more unsaturated bonds in its chain, optionally interrupted by one —O— or —CO— group, and optionally carrying one or more —X or —CX₃ substituent; or
   a saturated, unsaturated or aromatic carbocyclic group containing 3 to 8 carbon atoms, optionally carrying one or more halogen atom.

13. A process according to claim 10, wherein the carboxylic acid anhydride is a non cyclic anhydride wherein groups R$_a$ and R$_b$, which are identical or different, represent:
   a linear or branched acyclic aliphatic group comprising 1 to 12 carbon atoms, saturated or comprising 1 to 3 unsaturated double bonds, optionally interrupted by one —O— or —CO— group, and optionally carrying one or more —X or —CX₃ substituent; or
   a saturated, unsaturated or aromatic carbocyclic group containing 6 carbon atoms, optionally carrying one or more chlorine or bromine atom.

14. A process according to claim 10, wherein the carboxylic acid anhydride is acetic anhydride.

15. A process according to claim 1, wherein the quantity of base, expressed as the ratio between the number of moles of base and the number of moles of starting aromatic compound, is of from 0.05 to 1.0.

16. A process according to claim 15, wherein the quantity of base is of from 0.1 to 0.2.

17. A process according to claim 2, wherein the quantity of carboxylic acid anhydride is such that the mole ratio between the carboxylic acid anhydride and the starting aromatic compound is of from 2 to 10.

18. A process according to claim 1, wherein cyclising is carried out in the presence or absence of an organic solvent.

19. A process according to claim 18, wherein cyclising is carried out in the presence of an organic solvent selected from the group consisting of:

aromatic hydrocarbons, halogenated or not, aliphatic, cycloaliphatic or aromatic ether-oxides, linear or cyclic carboxamides, dimethylsulphoxide (DMSO);

hexamethylphosphotriamide (HMPT);

tetramethylurea;

nitro compounds;

aliphatic or aromatic nitriles;

tetramethylene sulphone (sulpholane); and mixtures thereof.

20. A process according to claim 18, wherein cyclising is carried out in the presence of an organic solvent being dimethylformamide.

21. A process according to claim 18, wherein the quantity of carboxylic acid anhydride is such that the mole ratio between the carboxylic acid anhydride and the starting aromatic compound is of from 1 to 3.

22. A process according to claim 18, wherein cyclising is carried out in the presence of an organic solvent, the quantity of organic solvent being such that the concentration of starting aromatic compound in the organic solvent is of from 1 to 5 mole/liter.

23. A process according to claim 22, wherein the concentration of starting aromatic compound in the organic solvent is of from 2 to 3 mole/liter.

24. A process according to claim 1, wherein cyclisation is carried out at a temperature of from 50° C. to 160° C.

25. A process according to claim 24, wherein the temperature is of from 100° C. to 140° C.

26. A process according to claim 1, wherein a cyclised product is obtained and wherein the process comprises the step of recovering it in an organic phase.

27. A process according claim 2, wherein the process comprises the step of, prior to cyclising, saponifying a compound with formula (I) comprising a group $COOR_2$ ester function in place of a carboxylic function COOH.

28. A process according claim 26, wherein the cyclised product has the following formula (V):

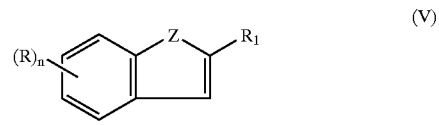

(V)

wherein R, $R_1$, Z and n have the meanings given claim 2.

29. A process according claim 26, wherein the cyclised product has the following formula (V'):

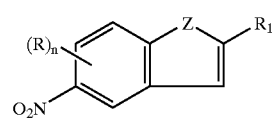

V' wherein R, $R_1$, Z and n have the meanings given claim 5.

30. A process according to claim 29, wherein the cyclised product is 2-n-butyl-5-nitrobenzofuran.

* * * * *